(12) United States Patent
Peltier

(10) Patent No.: US 9,983,222 B2
(45) Date of Patent: May 29, 2018

(54) AUTOMATIC PROCESS AND AUTOMATED DEVICE FOR PREPARING AND ANALYSING A PLURALITY OF CELL SUSPENSIONS

(75) Inventor: Eric Peltier, Clamart (FR)

(73) Assignee: NOVACYT, Velizy Villacoublay (FR)

( * ) Notice: Subject to any disclaimer, the term of this patent is extended or adjusted under 35 U.S.C. 154(b) by 647 days.

(21) Appl. No.: 13/636,665

(22) PCT Filed: Mar. 21, 2011

(86) PCT No.: PCT/FR2011/050575
§ 371 (c)(1),
(2), (4) Date: Oct. 24, 2012

(87) PCT Pub. No.: WO2011/117523
PCT Pub. Date: Sep. 29, 2011

(65) Prior Publication Data
US 2013/0034874 A1    Feb. 7, 2013

(30) Foreign Application Priority Data

Mar. 22, 2010    (FR) ...................................... 10 52049

(51) Int. Cl.
| C12Q 1/02 | (2006.01) |
| C12Q 1/24 | (2006.01) |
| G01N 35/10 | (2006.01) |
| G01N 1/31 | (2006.01) |
| G01N 1/28 | (2006.01) |

(52) U.S. Cl.
CPC ............. *G01N 35/10* (2013.01); *G01N 1/312* (2013.01); *G01N 2001/2846* (2013.01); *G01N 2035/106* (2013.01)

(58) Field of Classification Search
None
See application file for complete search history.

(56) References Cited

U.S. PATENT DOCUMENTS

| 3,525,591 | A | * | 8/1970 | Jungner et al. ................. 422/66 |
| 4,268,268 | A | * | 5/1981 | Blum ............................... 436/52 |
| 4,554,839 | A | * | 11/1985 | Hewett et al. ............. 73/864.16 |
| 5,092,184 | A | * | 3/1992 | Goodell et al. ............ 73/863.32 |
| 5,318,749 | A | * | 6/1994 | Eberle ............................. 422/72 |
| 5,408,891 | A | * | 4/1995 | Barber et al. ............. 73/864.22 |
| 6,174,678 | B1 | * | 1/2001 | Menzel et al. ............. 435/6.12 |
| 6,627,158 | B1 | * | 9/2003 | Peltier ........................... 422/501 |
| 8,478,018 | B2 | * | 7/2013 | Peltier ........................... 382/133 |
| 2002/0023884 | A1 | * | 2/2002 | Anderson ...................... 210/787 |
| 2003/0059343 | A1 | * | 3/2003 | Anderson ........................ 422/99 |
| 2004/0086494 | A1 | * | 5/2004 | John ........................... 424/93.21 |
| 2004/0229368 | A1 | * | 11/2004 | Rubio et al. ...................... 436/63 |
| 2007/0238169 | A1 | * | 10/2007 | Abilez et al. ................. 435/325 |
| 2010/0089925 | A1 | * | 4/2010 | Peltier ........................... 220/288 |
| 2010/0178689 | A1 | * | 7/2010 | Peltier ........................ 435/287.1 |

FOREIGN PATENT DOCUMENTS

| EP | 0527059 A1 | 2/1993 |
| EP | 0 590 506 A1 | 4/1994 |
| EP | 1 739 402 A1 | 1/2007 |
| FR | 2922019 A1 | 4/2009 |
| WO | WO 2006/058989 A1 | 6/2006 |
| WO | WO 2008/104710 A2 | 9/2008 |
| WO | WO 2009/156661 A1 | 12/2009 |

OTHER PUBLICATIONS

Merriam-Webster Dictionary, "bottle" (Accessed Feb. 6, 2014).*
Wakeman et al., Human Adult Stem Cells, vol. VII, Ch. 1, pp. 1-44 (2009).*
Fankhauser, 2009, <http://biology.clc.uc.edu/fankhauser/labs/genetics/buccal_dna_isolation/DNA_from_buccal_cells.htm> (Accessed Feb. 17, 2016).*
Laboratory Manual, 2008, <http://bioserv.fiu.edu/~biolab/labs/1010/fall%202008/Task%20Sheets%20Fall%202008/Week%208 %20-%20Biotechnology-%208th%20edition.htm> (Accessed Feb. 17, 2016).*

* cited by examiner

*Primary Examiner* — Thomas J. Visone
(74) *Attorney, Agent, or Firm* — Knobbe, Martens, Olson & Bear, LLP

(57) ABSTRACT

The present invention relates to a process for preparing and analyzing a plurality of cell suspensions (5) comprising at least the following successive steps:
(a) loading a plurality of bottles (4) onto a reception plate (6), each bottle (4) comprising a cell suspension (5) to be analyzed;
(b) loading a plurality of analysis containers (32, 34, 36) onto the reception plate (6); and
(c) taking a sample of a cell suspension (5) from a bottle (4) and depositing this sample in an analysis container (34, 36); wherein step (c) is repeated for each bottle (4) to be analyzed.
Step (c) of taking a sample of a cell suspension from a bottle (4) and depositing this sample in an analysis container (34, 36) comprises at least one step of breaking up the cell clusters by virtue of pipetting distribution means (20).
The invention also relates to an automated device for implementing this process.

10 Claims, 7 Drawing Sheets

AUTOMATIC PROCESS AND AUTOMATED DEVICE FOR PREPARING AND ANALYSING A PLURALITY OF CELL SUSPENSIONS

The present invention relates to a process for preparing and analysing a plurality of cell suspensions, of the type comprising at least the following successive steps:

(a) loading a plurality of sample containers onto a platform, each bottle comprising a cell suspension to be analysed;

(b) loading a plurality of analysis containers onto the platform; and (c) taking a sample of a cell suspension from a bottle and depositing this sample in an analysis container; step (c) being repeated for each bottle to be analysed.

The invention also relates to an automated preparative and analysis device for implementing this process.

The analysis of a cell suspension and for example of a fixed cytological smear is an extremely delicate operation. Cytological diagnosis covers diagnosis techniques which are based on morphological examination of cells. It is well adapted to the screening of cancer and pre-cancerous lesions in particular of the cervix.

The objective of such analysis is to screen for pathological cells, and hence a fully legible cell deposit representative of the region of interest must be obtained to avoid any diagnostic error.

To allow the analysis of a large number of samples and at a fast processing rate, it is sought to automate the preparation of samples for analysis and the actual analysis procedure. For this purpose, automated devices are known allowing analysis slides to be prepared from specimens such as smears and others.

An automated device of the aforementioned type is described for example in document US 2009/0233331.

However, such automated devices do not always allow the preparation of cell deposits permitting satisfactory analysis and leading to reliable diagnosis. Such automated equipment uses devices generating a certain numbers of artefacts entailing in particular filter management and pressure problems with changes in cell morphology and problems of filter mesh clogging with debris. In addition, handling operations differ depending on the type of sample: for example, red blood cells or mucus must perhaps first be removed before collecting the cells on the filter.

It is therefore not possible to implement a standardised method common to all types of gynaecological and non-gynaecological cytological samples, which limits action by operators to a minimum.

It is one of the objectives of the invention to overcome these disadvantages by fully automating the preparation and analysis of a plurality of cytological suspensions in reliable, reproductive and standardised manner and at a fast rate. Irrespective of the type of cytology, the preparation process is similar.

For this purpose, the subject of the invention is a process for sampling and analysing a plurality of cell suspensions such that step (c) of taking a sample of a cell suspension from a bottle and to depositing this sample in an analysis container comprises at least one step of breaking up cell clusters via pipetting-dispensing means.

According to other characteristics of the process:

step (c) of taking a sample of a cell suspension from a bottle and depositing this sample in an analysis container comprises at least one step of mixing and filtering the cell suspension in the bottle.

step (c) of taking a sample of a cell suspension from a bottle and depositing this sample in an analysis container further comprises at least the following steps:

(d) pipetting the sample up and down in the sample container to break up cell clusters;

(e) selecting relevant cells by differential decanting;

(f) aspirating a volume resulting from the differential decantation using pipetting means, the volume containing the sample to be analysed;

(g) homogenizing the aspirated sample in the pipetting means;

(h) moving the pipetting means to place them above the analysis container;

(i) dispensing the sample to be analysed into the analysis container.

each analysis container comprises a decanting well and an analysis slide placed facing the decanting well, and the process comprises at least the following successive steps:

(j) placing an absorption sheet on the loading plate so that each analysis slide is arranged between the loading plate and the absorption sheet;

(k) loading a plurality of decanting wells in a press and placing the press above the plate so that each decanting well is arranged above and facing an analysis slide; and (l) spreading a cell smear on the analysis slide, the cell smear resulting from the depositing of the sample in the decanting well;

the steps (j) and (k) being conducted after step (b) of loading a plurality of analysis containers and before step (c) of taking a sample of a cell suspension, and step (l) being conducted after step (c) of taking a sample of a cell suspension;

it comprises a step of analysising the cell deposit at the bottom of the decanting wells by measuring the cell density on the analysis slides;

it comprises an automated cell staining or labelling step;

it previously comprises a step to definitively seal the bottle containing the cell suspension to be analysed, the process being implemented without subsequent opening of the bottle; and each analysis container comprises a sampling or aliquoting tube.

A further subject of the invention is an automated device for sampling and analysing at least one cell suspension comprising:

at least one bottle containing the cell suspension to be analysed;

at least one platform on which the bottle is positioned and held fixedly and precisely in position;

at least one cell suspension decanting well; the decanting well is positioned and held fixedly and precisely on the plate;

an analysis system comprising at least one analysis slide intended to receive/contain a sample of the cell suspension, the sample being a volume portion of the cell suspension containing elements of interest to be analysed, and the analysis slide being positioned and held precisely and fixedly on the plate underneath and facing the decanting well;

the automated device comprises pipetting means capable of taking the sample of cell suspension from the bottle and of dispensing this sample into the decanting well on the analysis slide of the analysis system, these means being arranged to allow the breaking-up of cell clusters.

According to other characteristics of the automated device:
- it comprises a first mobile arm on which the pipetting means are attached, the said arm moving at least overhead the platform holding the sample containers, the decanting wells and the analysis slides;
- it comprises labelling or staining solutions which can be mixed with the cytological solution by the pipetting means;
- each bottle and each analysis slide comprises visual marking and the automated device comprises means for reading the visual markings;
- the reading means comprise a camera and are carried by a second mobile arm, the said second arm moving overhead at least the platform holding the sample containers, the decanting wells and the analysis slides;
- the bottle comprises filtering means arranged above a decanting cone, the pipetting means being arranged so that they can sample part of the cell suspension underneath the filtering means and re-inject the said part onto the decanting cone so as to mix the said cell suspension and to cause part of the said suspension to pass at least once through filtering means to break up those cell clusters having a size larger than the mesh size of the filter;
- the system for analysing the sample comprises means to analyse the cell density of the cell deposits at the bottom of the decanting well on the analysis slide;
- the means for analysing the cell density of the cell deposits at the bottom of the decanting well on the analysis slide comprise a camera;
- the system for analysing the sample comprises a device for forming a virtual slide of the sample;
- the device for forming a virtual slide of the sample comprises a camera;
- it comprises a single camera forming the reading means, the means for analysing cell density and the device for forming a virtual slide;
- it comprises a support comprising means for positioning at least the holder plate and capable of maintaining the plate fixedly and precisely, and a button capable of validating the position at least of the plate;
- it is arranged to implement the above process;
- the cell suspension is a cytological suspension; and
- the cytological suspension comprises a fixing solution containing between 80 and 95% by volume of:
  590 ml of physiological saline solution,
  10 ml of PEG,
  203 ml of iso-propyl alcohol,
  193 ml of pure ethanol,
  0.01% by volume of sodium azide,
  and between 20% and 5% by volume of 4% buffered formol.

The invention will be better understood on reading the following description given solely as an example with reference to the appended drawings in which.

With reference to the Figures, an automated device 2 is described for preparing and analysing a cell suspension which allows this preparation and this analysis to be automated.

Figure 1:
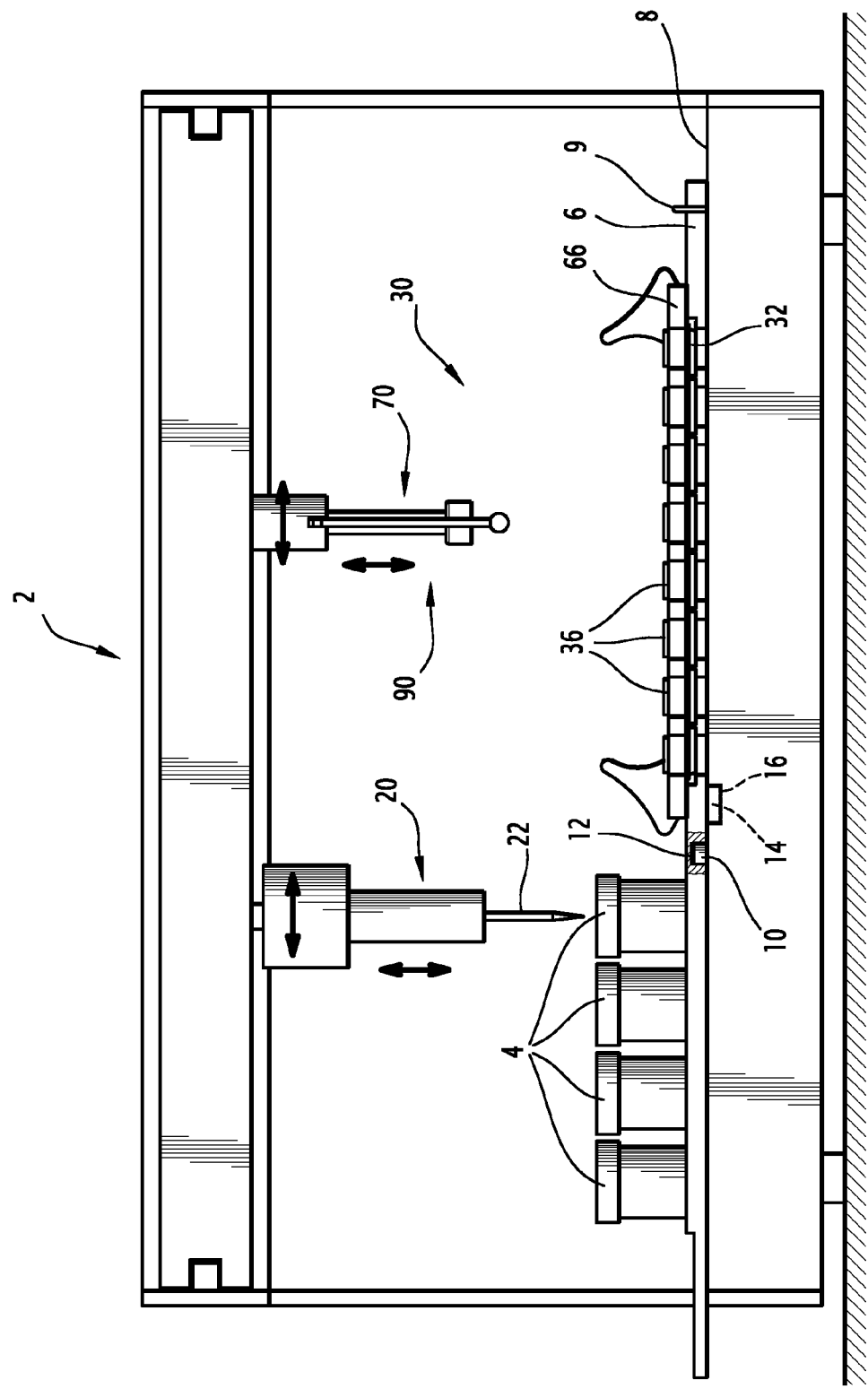
FIG. 1 is a schematic cross-sectional view of an automated sampling and analysis device according to the invention.
Figure 2:
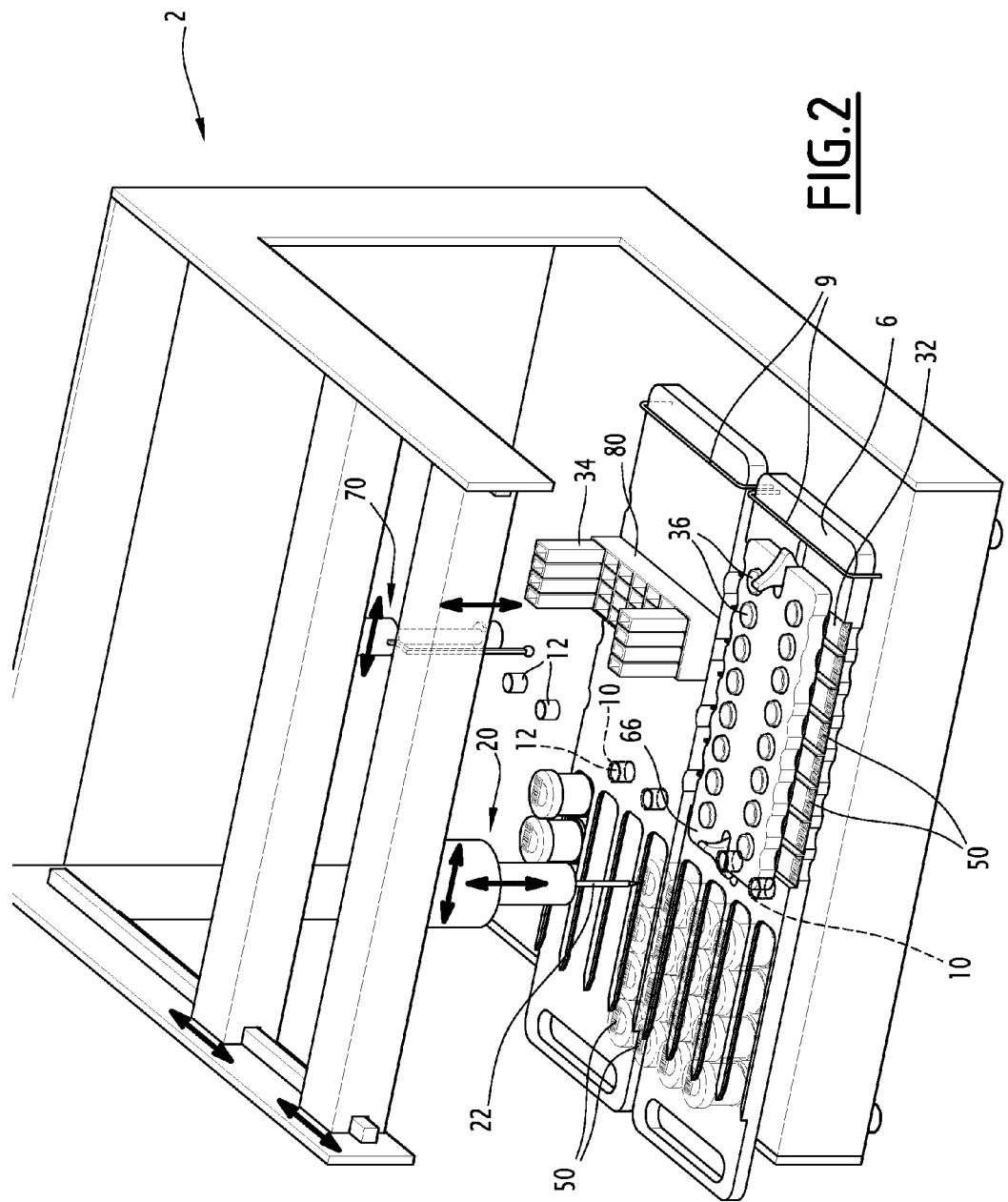
FIG. 2 is a schematic perspective view of the automated device shown in FIG. 1.

FIGS. 1 and 2 illustrate an automated device 2 for preparing and analysing at least one bottle 4 containing a cell suspension 5 to be analysed, such as a fixed cytological suspension for example.

Said cytological suspension 5 may derive from a cervical smear for example performed using a sampling brush (not illustrated). This cytological suspension particularly comprises cells.

The brush is then immersed in a bottle 4 containing a fixing solution and rubbed against a filter to extract and collect the cells and thereby form the cell suspension 5.

The fixer or fixing solution is intended to preserve and store cytological cell-containing samples or specimens for their subsequent analysis by a cytologist. Therefore the fixing solution must maintain the integrity of the nucleated cells and red blood cells, in particular their morphology, in the state in which they were before sampling.

The fixing solution is intended to preserve a cytological sample in vitro which contains biological cells intended to be analysed by a cytologist.

As already known and published by Saccomanno et al the alcohol fixing solution may also contain Carbowax® or Polyethylene Glycol (PEG). As is known and already published, formaldehyde can be associated with decalcifying or anti-aggregating agents such as ethylene diamine tetraacetic acid (EDTA) and the salts thereof. In addition, as is known and already published a mucolytic agent such as dithiothreitol (DTT) or acetylcystein can be added to mucus-containing samples.

Formaldehyde is used to preserve the red blood cells and nucleated cells without lysis thereof, thereby guaranteeing a reference in terms of size to allow more relevant diagnosis by the cytologist.

The following example illustrates the fixing solution without limiting the scope thereof:

EXAMPLE

Solution containing 80% by volume of:
590 ml of physiological saline solution,
10 ml of PEG,
203 ml of isopropyl alcohol,
193 ml of pure ethanol,
0.01% by volume of sodium azide,
and 20% by volume of 4% buffered formaldehyde.

The fixing solution of the invention does not contain any acetone or compounds from the family of ketones or any acetic acid since these products cause lysis of the red blood cells which, on bursting, release haemoglobin which attaches itself to the cells. Some types of staining such as Papanicolaou staining, owing to the complexity of the staining agents associating several nuclear staining agents with haemoglobin, make cytological analysis and particularly nuclear analysis very difficult and even impossible. Similarly, immune-chemical studies are often hampered by deposits of haemoglobin.

According to the invention, subsequent analyses of the sample by Papanicolaou staining or immuno-cyto-chemical studies of the sample fixed in the fixing solution described herein not containing any acetone or compounds from the ketone family or acetic acid, are improved.

The fixing solution described above therefore allows excellent preserving of the integrity of the nucleated cells and red blood cells in view of the analysis thereof.

In addition, the above-described fixing solution containing PEG and/or formaldehyde has a different density to conventional fixing solutions used in cytology, which are essentially alcohol-based. The Applicant has ascertained that the fixing solution therefore allows the selection of cells of interest via a density gradient in a manner that is more efficient than with conventional fixing solutions used in cytology.

The automated device 2 further comprises at least one platform 6 carrying at least the bottle 4 containing the cell suspension 5 to be analysed and a support 8 on which the platform 6 is arranged.

Figure 3:
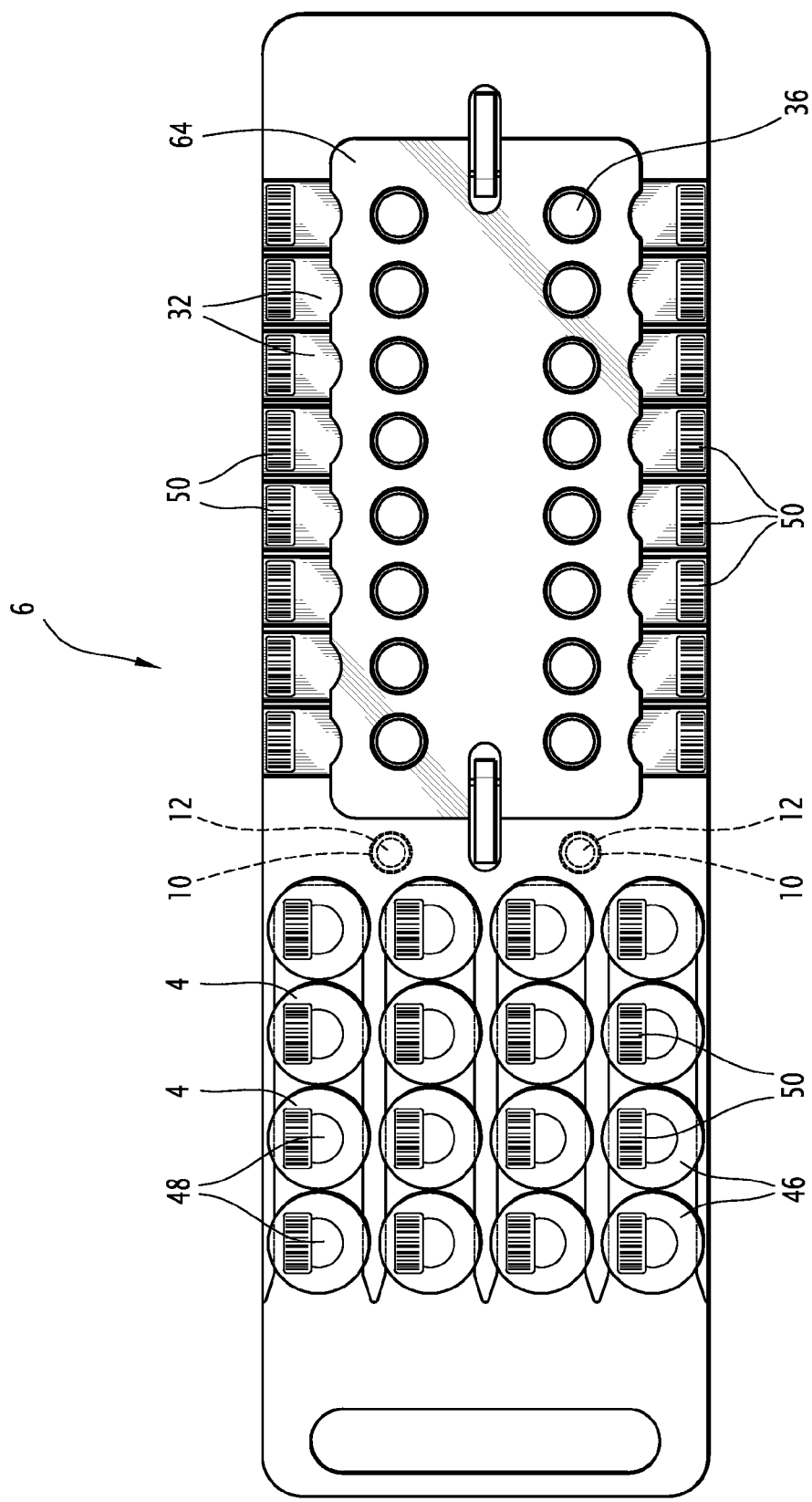
FIG. 3 is a schematic overhead view of a platform for the preparative and analysis automated device receiving sample containers each containing a cell suspension.

The platform 6 is intended to support a plurality of sample containers 4 each containing a cell suspension 5 to achieve rapid, automated preparation of a plurality of cell suspensions 5 to be analysed, in simultaneous or sequential manner of all or part of the suspensions. Said platform 4 has already been described in patent application EP-2 111 300, filed by the applicant, and allows the positioning and the precise and fixed holding in place of at least the bottle 4 on the plate 6. Persons skilled in the art can refer to this document and this plate will therefore not be described in more detail herein. A schematic view of the plate is shown in FIG. 3.

The support 8 comprises means for positioning the plate 6 capable of holding the plate fixedly and precisely in the automated device 2. These positioning means comprise means 9 for receiving an end part of the plate 6, the plate being arranged against or in the said means 9 when it is positioned in the automated device 2.

In addition, the plate 6 comprises positioning means on the support 8. These positioning means comprise at least one orifice 10 hollowed out of the thickness of the plate without passing through it and intended for the precise fixing of the plate on the support 8 of the automated device 2. Preferably, the plate 6 comprises two identical orifices 10 arranged orthogonally to the longest side of the plate 4.

The support 8 of the automated device 2 comprises positioning means mating with those of the plate 6. These means comprise at least one lug 12 and preferably as many lugs as orifices 10 of the plate 6. The shape of the lug 12 mates with the shape of the orifice 10 of the plate and is of slightly smaller size so that, when the plate 6 is positioned on the support 8, the lug 12 is located inside the corresponding orifice 10. Therefore the plate 6 is held fixedly and precisely on the support 8.

Also, the support 8 of the automated device 2 comprises a button 14 or pushbutton intended to validate the proper horizontal positioning of the plate 6 on the support 8. When the plate 6 is properly positioned i.e. when the entirety of the underside of the plate is in contact with the support 8, since the lugs 12 are received in the orifices 10, the pushbutton 14 is pressed into the support 8 in a space 16 provide for this purpose, thereby ensuring the proper positioning of the plate 6 and permitting the functioning of the automated device 2. When the pushbutton 14 is not pressed down the automated device is prevented from functioning.

Additionally the automated device 2 comprises pipetting-dispensing means 20 called pipetting or sampling means hereinafter, i.e. allowing the sampling and/or dispensing and/or filling of a sample of cell suspension 5. These pipetting means 20 extend above the platform 6. The sample is a precise volume portion of the cell suspension 5 containing elements of interest to be analysed e.g. cells.

These pipetting means 20 are mobile so that they can move above each bottle 4 for sampling and/or filling as illustrated by the arrows in FIG. 1. The pipetting means 20 are formed of at least one pipette 22 or needle and preferably a plurality of pipettes for example four or eight, arranged in parallel so that it is possible simultaneously to take samples from a plurality of sample containers 4 and to prepare these simultaneously in view of the analysis thereof.

The pipetting means 20 are attached to a first robotised arm that is mobile on the automated device 2 above the plates 6.

The device (orifices 10/lugs 12 and pushbutton 14) ensuring the precise positioning of the plate makes it possible to avoid breakage of the needles or pipettes 22 by preventing them from striking the edge of the sample containers 4, which could occur if the plate was ill-positioned in relation to the pipetting means 20. This therefore avoids additional costs for technical servicing to replace broken or deformed equipment Also, the automated device 2 comprises a preparative and analysis system 30 comprising at least one analysis support intended to receive/contain the sample of the cell suspension 5 sampled and dispensed into or onto the analysis support by the pipetting means 20.

For example, the analysis supports of this preparative and analysis system 20 may comprise smear slides 32, sampling or aliquoting tubes 34, analysis or decanting wells 36 depending on the analysis mode chosen by the practitioner.

The analysis supports 32, 34, 36 are held precisely and fixedly on the plate 6.

This preparative and analysis system 30 is described in more detail below.

The bottle 4 containing the cell suspension 5 to be analysed will now be detailed with reference to FIG. 4.

Preferably, this bottle 4 has the same characteristics as those described in document EP-2 111 300 so that it is possible to fix the bottle 4 on the platform 6, and some of the characteristics described in document WO-2006/058989 so that it is possible to prepare and analyse the cell suspension.

Figure 4:
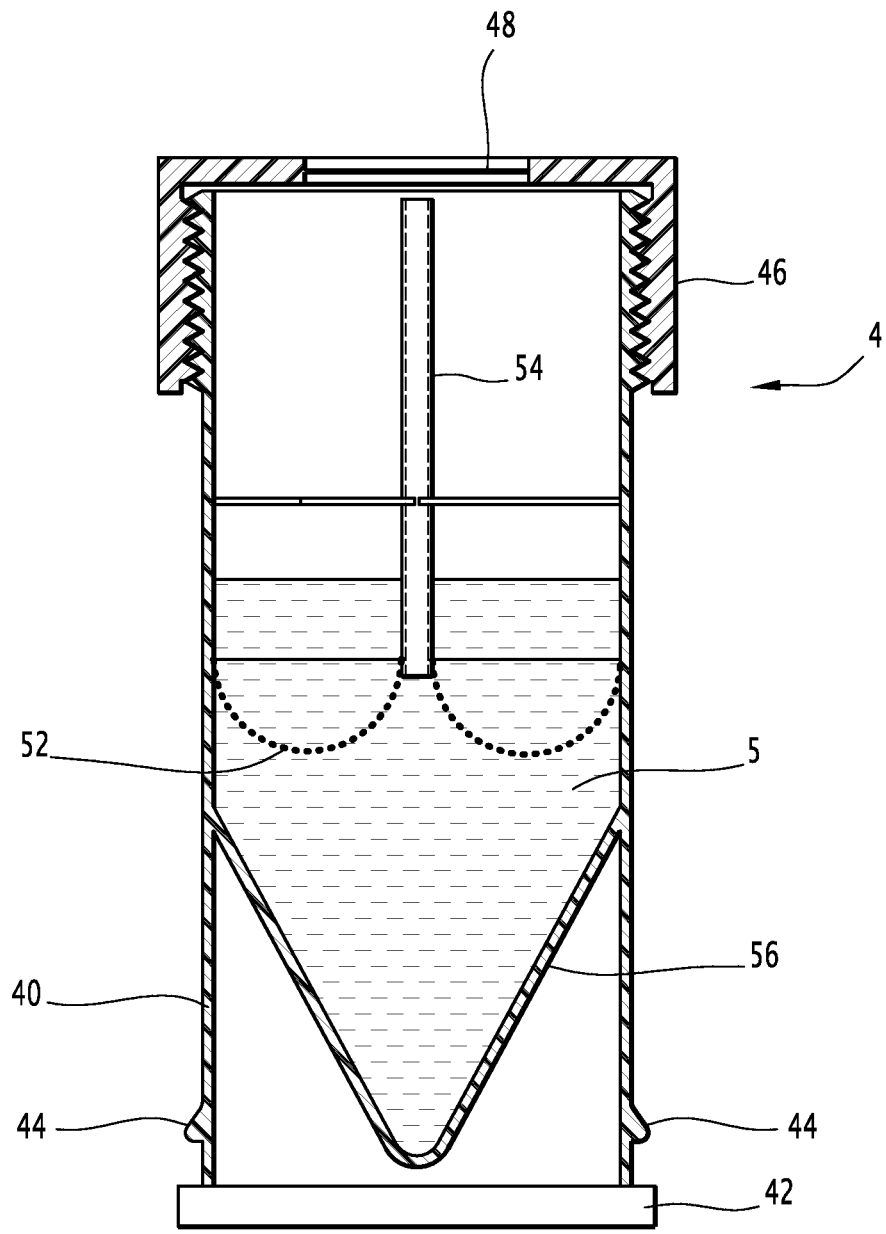
FIG. 4 is a cross-sectional view of a bottle intended to be received in the automated device.

With reference to FIG. 4, the bottle 4 containing cytological suspension 5 comprises a body 40 e.g. substantially cylindrical. From this body 40 there extends a lower edge 42 and blocking means 44 arranged on either side of the body and projecting therefrom allowing the blocking of the bottle 4 on the platform 6 as described in document EP-2 111 300 in longitudinal and elevation directions. The blocking means 44 are intended to engage in imprints of rails of the plate 6 so as to block the bottle 4 in a preferred direction. Persons skilled in the art can refer to this document to understand the functioning of this bottle 4 with the platform 6.

In addition, the bottle 4 also comprises a cap 46 for example provided with a membrane 48 which is piercable and self-healing allowing the passing of the pipetting means 10 of the automated device e.g. a pipette. This piercable and self-healing portion 48 particularly makes it possible not to remove the cap 46 from the bottle in order to take a sample of cell solution, and hence allows the preserved integrity of the sample by ensuring fully secure storage thereof after collection by the doctor or laboratory, remaining in a sealed bottle throughout the preparation and analysis process. In addition, this fully avoids any risk of contamination or inhalation of fixing solution for laboratory technicians.

The cap 46 of each bottle 4 further comprises visual marking 50 or identification intended to identify the cell suspension 5 contained in the bottle 4. For example, this visual marking 50 is a bar code. This identifier 50 provides for full traceability during preparation and analysis by computerized management of sample numbers.

According to other embodiments, the identification means are different and for example comprise a data-carrying label or an electronic chip of RFID chip type whose content can be remotely read by reading means.

According to one embodiment intended for the preparation of cytological samples requiring the use of a sampling brush, the bottle 4 is equipped with filtering means 52 at least partly immersed in the suspension such as described in document WO-2006/058989. These filtering means 52 are in the form of a filtering web of material forming a basket for example whose periphery is attached to the body 40 of the bottle and whose centre is connected to a tube 54 extending in the direction of the opening of the bottle, associated with means for holding the bottle in position and adapted to allow the cell solution sampling means 20 of the automated device to pass underneath the filtering means, in particular the pipette 22 for aspirating the suspension.

Preferably the web of filtering material is braided nylon, allowing detachment of the cells by mechanical action when the brush is rubbed over the material without damaging the specimen.

In addition, the lower part of the bottle 4 comprises a decanting cone 56.

Also, and in manner known per se, the bottle 4 is provided with an opening intended to receive a cytological sampling brush detachably attached onto a handle. The opening of the bottle comprises brush abutment means so that the brush can be blocked in the bottle and detached from the handle.

Persons skilled in the art can refer to this document for particular details of this bottle, which will not be further described herein. With said bottle it is possible to preserve the brush without hampering or breaking the sampling needle.

According to one embodiment intended for the preparation of cytological samples not requiring the use of a sampling brush, for example specimens of biopsy type or the collecting of fluids, the bottle 4 is equipped neither with a central tube nor with filtering means.

The preparative and analysis system 30 will now be described in detail.

Figure 5:
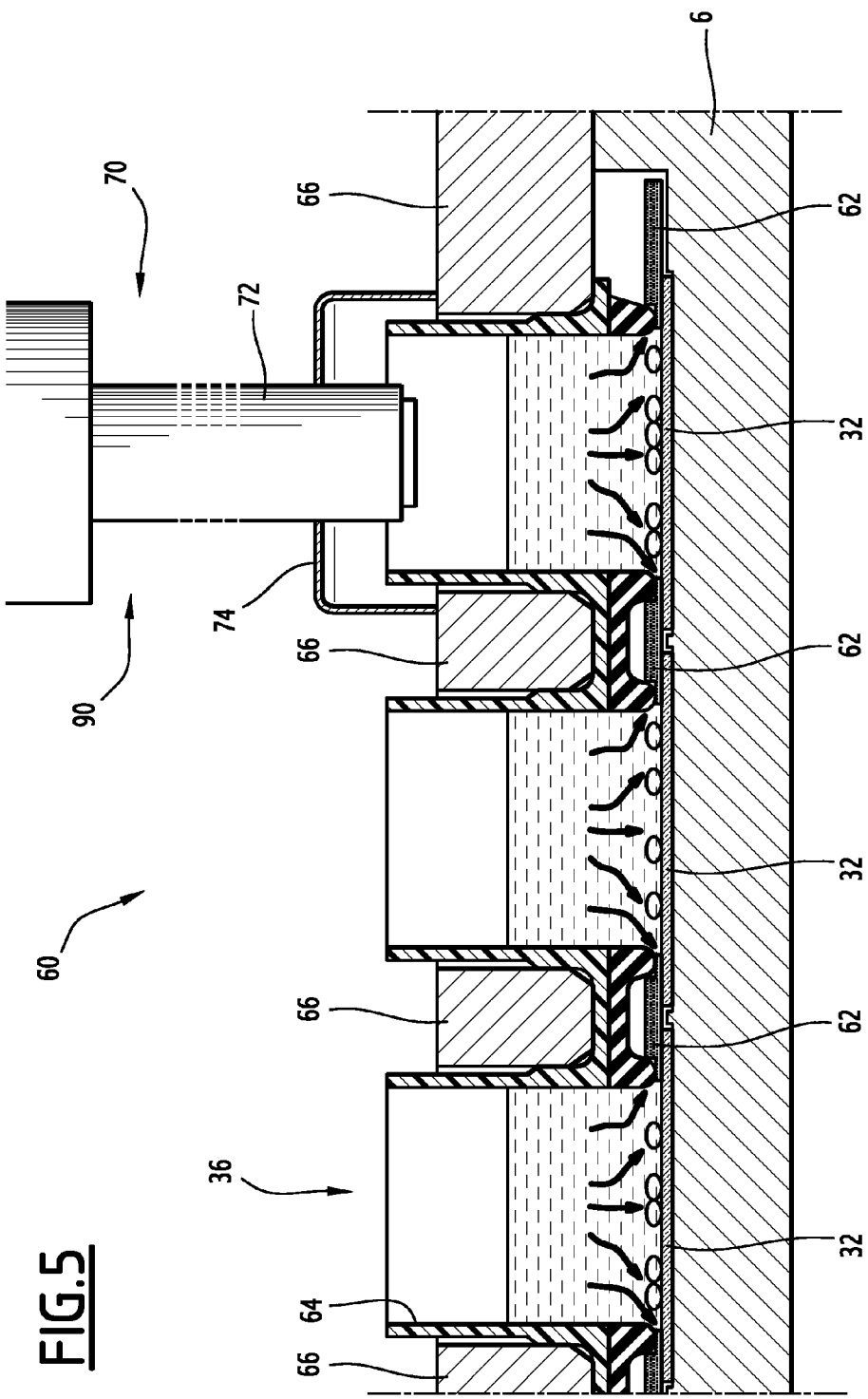
FIG. 5 is a cross-sectional view of a decanting well intended to be received in the automated device.

With reference to FIG. 5, the preparative and analysis system 30 preferably comprises a device 60 for depositing cells by decanting on an analysis slide. Said device 60 for depositing cells by decanting on an analysis slide has already been described in document FR-2 917 165 and reference thereto can be made by those skilled in the art.

This device 60 comprises at least one decanting well 36 placed above an analysis slide 32 and an absorbent material 62.

The analysis slide 32, at an end part, comprises identification means 50 for example visual marking of bar code type.

The suspension is dispensed using the pipetting means 20 into the receiving chamber 64 of the decanting well 36 placed above the analysis slide 32 and whose bottom part is open and extends opposite a cell depositing area of the analysis slide 32. The bottom of the chamber is in fluid communication with the absorbent material 62 of the preserving or fixing liquid for gradual absorbing thereof and to allow homogeneous depositing by decantation of the cells onto the cell depositing area of the analysis slide 32. In this manner, a uniform cell deposit is obtained within a shortened decanting time.

The absorbent material 62 is partly compressed by a decanting press 66 between the bottom of the receiving chamber and the analysis slide around the cell depositing area.

Figure 6:
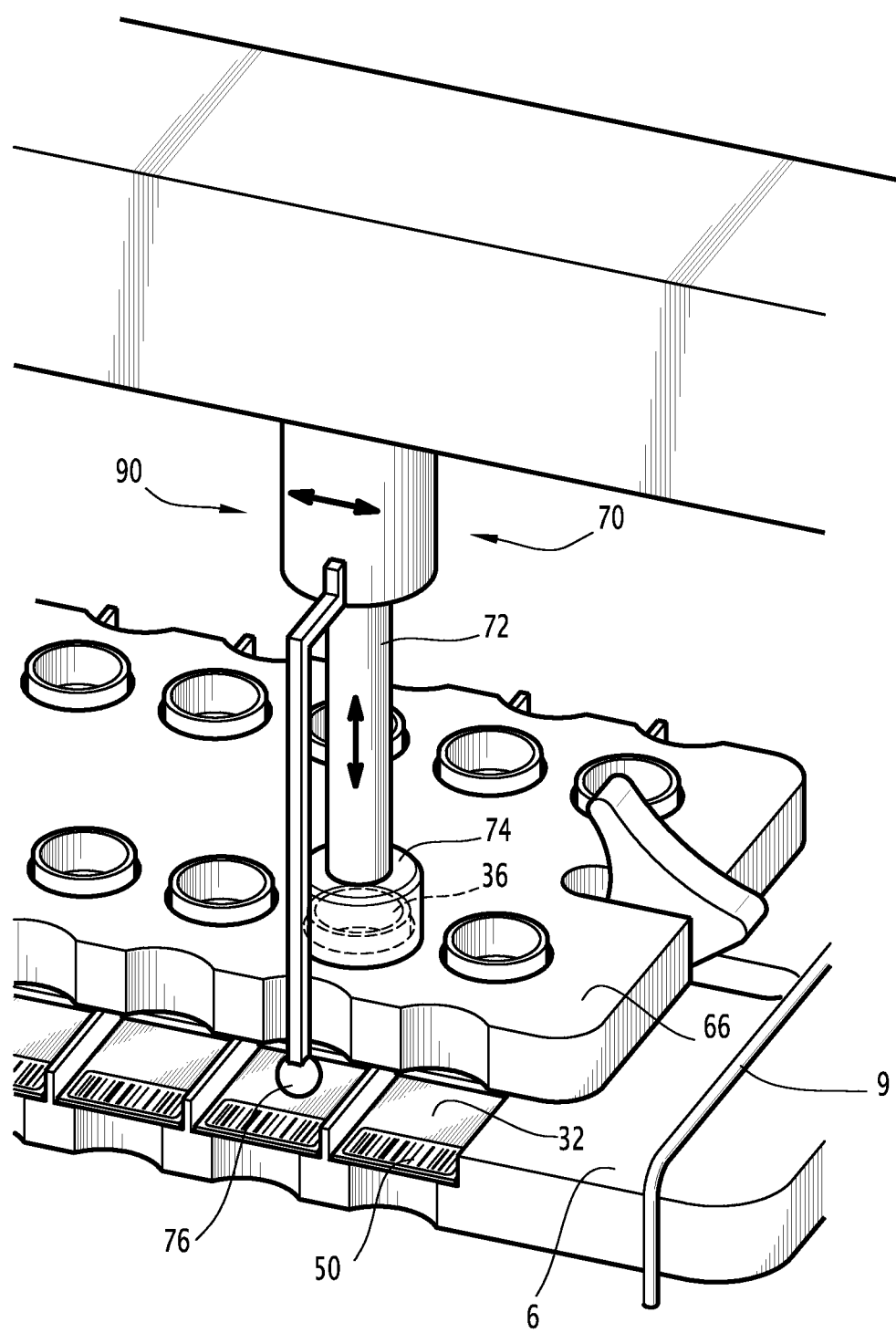
FIG. 6 is a schematic perspective view of the analysis means of the automated device in FIGS. 1 and 2.

With regard to FIGS. 5 and 6, the preparative and analysis system 30 comprises means 70 for measuring cell density in the decanting chamber, so as to form an analysis slide 32. Said cell density measuring means 70 are described in document FR 2 922 019 to which persons skilled in the art may refer.

Therefore the cell density measuring means 70 comprise a camera 72 arranged to record images of the plate 6 i.e. of the content of the decanting chamber 64 and of the analysis slide 32.

In addition, the cell density measuring means 70 comprise a sleeve 74 attached around the camera so that when the camera 72 is lowered and placed above the decanting chamber 64 to acquire images of the content of this chamber, this sleeve 74 is in contact with the decanting press 66 and forms a dark room obtaining light imperviousness to optimise the quality of image acquisition.

The cell density measuring means 70 further comprise means for illuminating the decanting chamber to enable the camera 72 to perform cell density measurement. These illuminating means comprise a light source 76 for example attached to the camera 72. When the camera 72 is lowered, the light source 76 is brought as close as possible to the edge of the analysis slide 32 to obtain optimal light transmission. The light source 76 then diffuses light into the analysis slide 32.

The cell density measuring means 70 are attached onto a second robotised arm mobile above the sample containers 4 of the plates 6.

According to one variant, the analysis supports of this system 30 comprise at least one sampling or aliquoting tube 34 and a support 80 in which a plurality of tubes 34 can be inserted so that they can be held fixedly in position. This support 80 of the aliquoting tubes 34 can be precisely attached onto the plate 6 so that the pipetting means 20 can take samples of the cytological solutions 5 contained in the sample containers 4 and dispense these into aliquoting tubes 34, the sample containers being fixed on the same plate as the aliquoting tubes.

The two possibilities, one corresponding to the decanting well 36 placed over an analysis slide 32 and with an absorbent material 62, and the other to the sampling or aliquoting tube 34, can be associated on one same carrier for simultaneous or staggered performing of complementary techniques either systematically or in correlation with the results of density analysis on a non-stained slide allowing better control over the pre-analytical step.

The automated device 2 further comprises remote reading means 90 intended to identify the visual marking 32 on the sample containers 4. These reading means 90 comprise a wide field camera and extend above the platform 6. These remote reading means 90 are carried by a second mobile robotised arm of the automated device, the second arm moving from one bottle 4 to the next fixedly held in position on the plate 6 to perform reading of the visual marking 50 or identifier marked on the cap 46.

The camera is positioned so that it is able to read the identification data 50 of the analysis slide 32. This data is transmitted for example to a data processing system ensuring quality monitoring of a plurality of analysis slides and the grouping of data on the cell smear deposited on this slide. This data particularly comprises the origin of the cell smear, the marking of the analysis slide being paired with the marking on the sample containers 4.

According to one preferred embodiment, the camera 72 of the cell density analysis means 70 allows the reading of the visual markings 50. In this manner the cell density analysis means 70 and the remote reading means 90 are combined, providing for savings in space.

Preferably the markings 50 are oriented in a precise, invariable direction when the cap is fixed onto the body, which allows easy use of the remote means 90 for reading the markings. Invariable orientation can be obtained via the means 44 for blocking the bottle 4 described in document EP-2 111 300.

These remote reading means 90, on account of the specific orientation of the sample containers 4, allow unitary or multiple viewing of these sample containers so that they can be matched in unitary or multiple fashion with the envisaged analysis system (smear slides 32, sampling or aliquoting tubes 34, analysis well 36 . . . ) this system itself being fixedly positioned. In other words, the reading means 90 allow the reading of the marking 50 of a single bottle 4 or of several markings at the same time. This fixed positioning, which corresponds for example to analysis slides 32 positioned in the decanting press 66, lies in the continuation of the rails described in document EP-2 111 300 acting as support for the sample containers 4, so that one same single plate allows the proper positioning of the sample containers 4 and of the slides 32 for the remote reading means, and offers unitary or multiple viewing. Therefore grouped processing of the sample containers is possible which provides for a faster analysis rate.

The automated device further comprises a processor, not illustrated, to collect the choices of parameters set by the user in relation to the type of cytological sample, and to control the robotised arms, the pipetting means 20, the reading means 90, the cell density analysis means 70, the pushbutton 14 (movements, sampled volumes, camera acquisition, light source . . . ).

According to one embodiment, the automated device further comprises a support, not illustrated, fixed in precise manner on the support 8 of the automated device 2 and which comprises containers containing solutions generally used for staining or labelling specific entities of cells such as nuclei, cytoplasms or other constituent elements of a cell. This support for staining or «labelling» solutions allows staining or labelling steps to be conducted on the analysis slides such as routinely performed by persons skilled in the art. This staining or labelling step is then carried out using the pipetting means 20 which, after being positioned overhead the containers of staining or labelling solutions, take up the necessary volume and they are then moved to above the analysis slides where the pipetting means dispense their content.

According to one embodiment, the analysis system 30 of the automated device 2 further comprises a device for forming a virtual slide of the sample such as described in document FR-2 931 966 and comprising a camera. According to one embodiment, the same camera as for the analysis means and/or reading means is used.

The automated device then comprises a single camera forming the reading means 90, the cell density analysis means 70 and the device for forming a virtual slide, allowing savings in space.

The process for preparing and analysing these suspensions implemented by the automated device 2 described above will now be further detailed for the preparation of analysis slides 32.

Beforehand, after taking the cell samples 5 to be prepared and analysed and after transferring these into sample containers 4, the practitioner definitively seals the sample containers 4 with their caps 46. The process for preparing and analysing these suspensions is effectively implemented without any subsequent opening of the sample containers 4.

In another embodiment, if a cytological sample is taken by puncture using a fine needle (Fine Needle Aspiration), the practitioner can insert the cell sample by inserting the sampling needle through the self-healing membrane of the bottle without having to open the cap at any time.

The technician or user, after a sufficient cell fixing time e.g. at least two hours, then loads the sample containers 4 with cell suspensions 5 onto the loading plate 6 and as many containers of the analysis system 30, preferably analysis slides 32.

The absorbent sheet 62 is then placed on the plate 6 so that each analysis slide 32 is arranged between the loading plate 6 and the absorption sheet 62. A plurality of decanting wells 36 are loaded in a decanting press 66. The decanting press 66 is installed above the plate 6 so that each decanting well 36 lies above an analysis slide 32 such as described in document FR-2 917 165.

The plates 6 are then loaded into the automated device 2 on the support 8 thereof and precisely fixed in position by means of the mating positioning means 10, 12 of the plates 6 and of the support 8 of the automated device 2, and by means of the pushbutton 14 which validates this positioning if it is correct.

The technician or user opens the software, chooses the very simple parameter settings in relation to the number and type of samples placed in the automated device and starts the preparation session.

The reading means 90 identify the visual markings 50 of the sample containers 4 and of the analysis slides 32 allowing a correlation to be determined between the sample containers 4 containing the solutions to be analysed and the analysis slides 32 to be prepared.

The sampling means 20 are placed above the bottle 4 containing the cell solution 5 to be analysed. The needle or pipette 22 of the sampling means 20 passes through the self-healing membrane 48 of the cap 46 of the bottle 4 down to the cell suspension.

A sample of a cell suspension in a bottle 4 is then taken by the pipette 22 of the sampling means 20.

Figure 7:
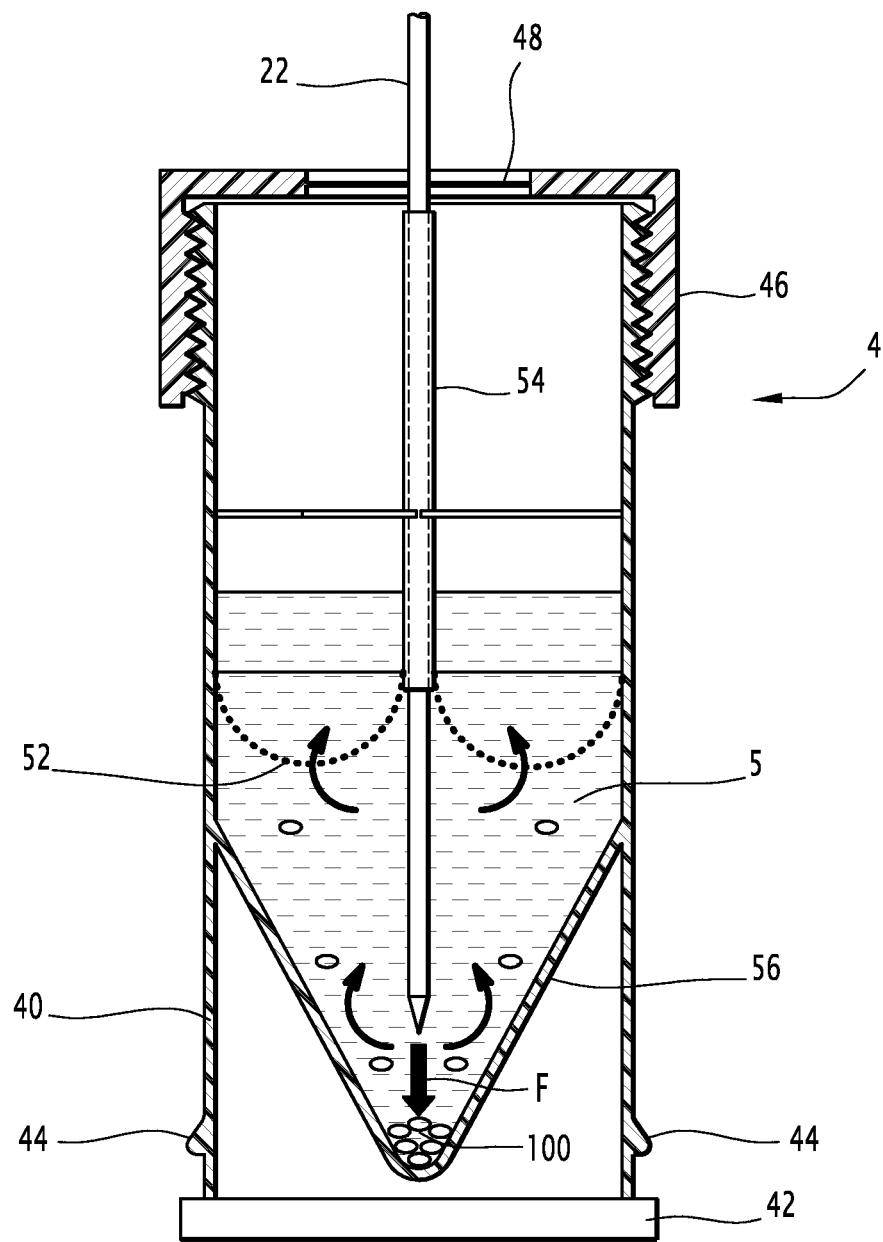
FIG. 7 is a cross-sectional view of a bottle during a mixing step of the process for preparing and analysing a cell suspension.

For this purpose, the cell suspension 5 is mixed in the analysis bottle 4 by the pipette 22 of the pipetting means 20 by aspirating/sampling a first volume of cell solution then expelling/ejecting the first volume into the cell solution, such as illustrated by the arrow F in FIG. 7. Preferably the first volume is substantially between 50 µL and 2000 µL of the cell solution. The objective of this step is to break up/fracture the cell clusters of the cytological sample 5 to be analysed on the wall of the decanting cone 56 of the bottle 4. Also, the cells re-injected into the bottle pass through the filtering means to break up the cell clusters having a larger size than the mesh size of the filter, which allows a second filtering of the sample to be obtained and the replacing in suspension of the sample.

Initial decanting of the cell solution is then performed for a first time period. Preferably the first time period is substantially between 5 minutes and 12 hours depending on the chosen analysis mode e.g. 15 minutes for the preparation of an analysis slide. With this step it is possible to obtain a gradient between the cells of interest to be analysed and inflammatory or haemorrhagic cells i.e. differential decanting.

An aspiration step of the solutions is next performed, these solutions being deposited in the analysis container. This step comprises i) the aspiration by the pipetting means 20 of a volume of glue adapted to cause the cells to adhere to the analysis slide 32 irrespective of type, or of buffer, ii) optionally a volume of air such as described in document FR 2 919 054, then iii) a volume of cell solution at the bottom of the decanting cone 56 containing relevant cells i.e. the cells located in the lower part of the solution after the first differential decanting.

Preferably, the volumes of glue and cell solution are equivalent and substantially between 50 µL and 1000 µL, for example 250 µL.

In the embodiment with aliquoting tubes the volume of glue is zero.

Also preferably, this last sampling step of a volume of cell solution is itself performed in two steps: a first sub-step called a «micro-mixing» step then a second sub-step to aspirate the desired volume of cell solution.

The «micro-mixing» step consists of aspirating a volume of cytological solution just above the bottom of the decanting cone of the bottle, for example at a distance of 2 mm, the volume being between 20 µL and 200 µL e.g. 100 µL, then the pipetting means 20 re-inject part of the sampled volume e.g. 50 µL, substantially at the same point to avoid a «dead volume or residue» 100, i.e. to detach the cells from the bottom of the decanting cone 56 via the injection force of the pipetting means 20 and to obtain highly localised replacing in suspension.

This «micro-mixing» step is optional and can be replaced by a simple sampling step of a volume of cytological solution.

The use of glue adapted to cause the cells to adhere to the analysis slides 32 allows the use of slides which have not been subjected to any specific treatment for cell adhesion, and thereby reduces the costs of preparation and analysis of the cytological solutions to be analysed.

For example, 250 µL of glue are taken and 100 µL of the cytological solution containing the cells of interest, then 50 µL of the cytological solution sample contained in the pipette are re-injected and 200 µL of the cytological solution are taken to have the same quantity of glue or buffer and of cells of interest.

The pipette 22 is then actuated automatically to mix the content thereof homogeneously i.e. the glue or buffer and the sampled cytological solution such as described in document FR 2 919 054. This step also allows the sample to be diluted and replaced in homogeneous suspension in the glue or buffer, following a diluting method such as described in document FR-2 919 054.

In another embodiment, the buffer solution can be completed with labelling or staining elements.

The pipetting means 20 are then moved to above a decanting well 36 to dispense/deposit the sample in the decanting chamber 64 and to form an analysis slide 32 comprising a cell smear to be analysed. The cell smear results from the depositing of the sample in the decanting well such as described in document FR-2 917 165 to which reference may be made by persons skilled in the art.

A second decanting is conducted on the slide for a second time period. Preferably, the second time period is substantially between 5 and 60 minutes and is preferably 15 minutes for the preparation of an analysis slide.

The sampling step and slide 32 forming step are repeated for each bottle 4 to be analysed, by differentially selecting pathological and relevant cells needed for diagnosis by the cytologist.

A step to analyse the deposit of cells at the bottom of the decanting well 36 is then carried out by measuring the cell density on the analysis slides 32, in order to propose a pre-analytical inspection of all samples whether intended for cytological analysis or for additional biological techniques, for example such as described in document FR-2 922 019. This step is used to determine whether the cell suspension contains a sufficient number of cells to obtain a satisfactory cell deposit able to lead to reliable diagnosis, so that it is possible automatically to readjust the sample in order to obtain a suitable cell density for analysis of the slide 32. This step allows the ensured quality monitoring of the analysis slide 32 prepared from the cell solution 5.

According to one embodiment, this analysis step of the cell deposit is followed by an automated staining or labelling step.

According to one embodiment, the pipetting means 20 comprise a plurality of needles, preferably four or eight, allowing the preparation and analysis of a plurality of cell suspensions in parallel, and an increase in the rate of preparation of analysis slides.

The automated device of the invention allows the automated performing of smears and other thin layer cytological sampling.

One of the advantages of the automated device 2 of the invention is that it is entirely sealed, from the bottle 4 to the analysis slide 32, thereby ensuring the integrity of all the solutions and cytological specimens, fully avoiding risks of contamination and ensuring greater practitioner safety (no inhaling of the fixing solution). This advantage also results from the use of a bottle combining filtering means and decanting means to obtain thin layer cytological smears.

Additionally, contrary to automated devices such as the one described in document US 2009/0233331, the sample containers 4 are fixedly held on the support of the automated device 2, it is the other systems such as the pipetting means 20, the reading means 70 and the density analysis means 90 which are mobile above the sample containers 4 ensuring greater safety of handling at the laboratory.

In addition, it allows better standardisation. All the samples are effectively taken:
 at the same point to within one tenth of a millimeter in the decanting cones of the sample containers, through the precise, fixed positioning of the plates comprising the sample containers and other containers (analysis slides, aliquoting tubes, decanting wells);
 in the same quantity to within one microliter via the pipetting means; and
 at the same time, since all the samples are taken following the same method.

In addition, complete traceability throughout analysis via computerized management of sample numbers is obtained by means of the visual markings 50 on the caps of the containers placed in correlation with those of the preparation containers such as the analysis slides, using remote reading means of these visual markings.

The method for adjusting cell density implemented by the automated device to form analysis slides allows the relative density of pathological cells to be increased if necessary, whilst maintaining a streamlined but informative analysis context, and improving smear quality and preservation of the selected elements. This provides for more reliable interpretation compared with the traditional technique or with semi-automated thin layer cytology techniques.

In addition, the automated preparation of a container or group of containers simultaneously allows a significant reduction of 90% in the technical preparation time compared with the conventional technique or with semi-automated thin layer cytology techniques.

To conclude, the automation allows the setting up of a true quality assurance system and standardisation of thin layer deposit, improving the reproducibility of smears and ensuring heed of cell integrity and facilitated reading. It also allows a distinct reduction in technical and reading costs.

The invention claimed is:

1. A process for preparing and analyzing a plurality of cell suspensions comprising the following successive steps:
   (a) loading a plurality of sample containers on a platform, each sample container comprising a cell suspension to be analyzed;
   (b) loading a plurality of analysis containers on the platform;
   (c) pipetting sample up and down in each of the sample containers to break up cell clusters, wherein the cell clusters are broken up by ejecting and fracturing the cell clusters against a wall of the sample containers, thereby producing a cell suspension;
   (d) permitting cells in the cell suspension to settle in the sample container for a predetermined time period, wherein a gradient of cells of interest is established in the sample containers; and
   (e) selecting cells from each of the sample containers by differential decanting comprising:
      (i) at least one step of micro-mixing the cells in each of the sample containers, wherein a volume of solution is aspirated with a pipettor just above the bottom of a decanting cone of the sample containers and then reinjected at the same point to detach the cells from the bottom of the decanting cone, thereby eliminating any dead volume or residue of cells at the bottom of the decanting cone, and
      (ii) aspirating a volume of cells from a position in the gradient of cells in each of the sample containers.

2. The process according to claim 1, wherein step (c) comprises a step of mixing and filtering the cell suspension in the sample container.

3. The process according to claim 1, wherein step (e) further comprises the following steps:
   (f) homogenizing the aspirated samples in the pipettors;
   (g) moving the pipettors to positions above the analysis containers; and
   (h) dispensing the samples to be analyzed into the analysis containers.

4. The process according to claim 1, wherein each analysis container comprises a decanting well and an analysis slide placed facing the decanting well, and wherein the process comprises at least the following successive steps:
   (i) placing an absorption sheet on the platform, so that each analysis slide is arranged between the platform and the absorption sheet;
   (j) loading a plurality of decanting wells in a press and placing the press above the plate so that each decanting well is arranged above and facing the analysis slide; and
   (k) forming a cell analysis smear on the analysis slide, the cell smear originating from depositing of the sample in the decanting well;
   steps (i) and (j) being performed after step (b) of loading a plurality of analysis containers and before step (e)(ii) of aspirating a volume of cells, and step (k) being performed after step (e)(ii) of aspirating a volume of cells.

5. The process according to claim 4, further comprising a step of analyzing the deposit of cells at the bottom of the decanting wells by measuring the cell density on the analysis slides.

6. The process according to claim 1, further comprising an automated cell staining or labelling step.

7. The process according to claim 1 comprising a previous step of definitively sealing the bottle containing the cell suspension to be analyzed, the process being implemented without subsequent opening of the sample container.

8. The process according to claim 1, wherein each analysis container comprises an analysis support.

9. The process of claim 3, wherein, in step (e), the cells are permitted to settle in the sample container for a period 5 minutes to 12 hours.

10. The process of claim 8, wherein the analysis support is selected from the group consisting of a smear slide, a sampling tube, and a well.

* * * * *